United States Patent
Grueebler et al.

(10) Patent No.: US 10,406,027 B2
(45) Date of Patent: Sep. 10, 2019

(54) OCT TRANSPARENT SURGICAL INSTRUMENTS AND METHODS

(71) Applicant: Novartis AG, Basel (CH)

(72) Inventors: Reto Grueebler, Greifensee (CH); Philipp Schaller, Stein am Rhein (CH)

(73) Assignee: Novartis AG, Basel (CH)

( * ) Notice: Subject to any disclaimer, the term of this patent is extended or adjusted under 35 U.S.C. 154(b) by 132 days.

(21) Appl. No.: 14/464,491

(22) Filed: Aug. 20, 2014

(65) Prior Publication Data
US 2015/0359669 A1 Dec. 17, 2015

Related U.S. Application Data

(60) Provisional application No. 62/012,073, filed on Jun. 13, 2014.

(51) Int. Cl.
*A61F 9/00* (2006.01)
*A61F 9/007* (2006.01)
(Continued)

(52) U.S. Cl.
CPC .......... *A61F 9/00736* (2013.01); *A61B 17/30* (2013.01); *A61B 2017/00907* (2013.01);
(Continued)

(58) Field of Classification Search
CPC . A61F 9/007; A61B 17/30; A61B 2090/3735; A61B 2090/3937;
(Continued)

(56) References Cited

U.S. PATENT DOCUMENTS

| 1,294,284 A | * | 2/1919 | Logeman | A61B 17/30 606/131 |
| 1,443,086 A | * | 1/1923 | Muchow | A61B 17/30 294/99.2 |

(Continued)

FOREIGN PATENT DOCUMENTS

| JP | 2005-525893 A | 9/2005 |
| WO | 2013151879 A1 | 10/2013 |
| WO | 2014078049 A1 | 5/2014 |

OTHER PUBLICATIONS

International Search Report and Written Opinion of the International Searching Authority, International Application No. PCT/EP2015/062867, dated Aug. 25, 2015, 13 pages.

(Continued)

*Primary Examiner* — Alexander J Orkin

(57) ABSTRACT

An ophthalmic instrument includes a shaft comprising a lumen. The instrument also includes a first arm extending from the lumen, the first arm having a first distal portion having a first flat tip. The instrument also includes a second arm extending from the lumen, the second arm having a second distal portion having a second flat tip that is positioned such that the second flat tip contacts the first flat tip when the first arm is forced towards the second arm. The first arm and the second arm comprise at least in part, a first material that is substantially transparent to electromagnetic radiation having a wavelength within a range of about 700-1200 nanometers (nm) and is substantially opaque to electromagnetic radiation having a wavelength within a range of about 400-700 nm.

7 Claims, 7 Drawing Sheets

(51) Int. Cl.
*A61B 17/30* (2006.01)
*A61B 90/00* (2016.01)
*A61B 17/00* (2006.01)
*A61B 17/32* (2006.01)

(52) U.S. Cl.
CPC .............. *A61B 2017/305* (2013.01); *A61B 2017/320008* (2013.01); *A61B 2090/0817* (2016.02); *A61B 2090/3735* (2016.02); *A61B 2090/3937* (2016.02); *A61F 9/007* (2013.01)

(58) Field of Classification Search
CPC .... A61B 2090/3941; A61B 2090/3983; A61B 2017/00907; A61B 2017/305
See application file for complete search history.

(56) References Cited

U.S. PATENT DOCUMENTS

| | | | | |
|---|---|---|---|---|
| 3,404,677 | A * | 10/1968 | Springer | A61B 17/29 30/135 |
| 3,653,389 | A * | 4/1972 | Shannon | A61B 17/30 294/99.2 |
| 4,374,523 | A * | 2/1983 | Yoon | A61B 1/313 128/831 |
| 4,671,283 | A * | 6/1987 | Hoskin | A61B 17/30 606/211 |
| 5,258,005 | A * | 11/1993 | Christian | A61B 17/29 606/205 |
| 5,318,589 | A * | 6/1994 | Lichtman | A61B 17/29 600/564 |
| 6,517,554 | B1 * | 2/2003 | Zhu | A61B 17/30 606/150 |
| 6,616,683 | B1 * | 9/2003 | Toth | A61B 17/29 606/205 |
| 2002/0177873 | A1 * | 11/2002 | Diaz | A61B 17/12022 606/205 |
| 2004/0167391 | A1 * | 8/2004 | Solar | A61B 90/39 600/411 |
| 2005/0203554 | A1 * | 9/2005 | Dykes | A61B 90/39 606/166 |
| 2008/0243181 | A1 | 10/2008 | Schneider et al. | |
| 2010/0217297 | A1 | 8/2010 | Nevyas Wallace | |
| 2012/0184846 | A1 | 7/2012 | Izatt et al. | |
| 2013/0296694 | A1 | 11/2013 | Ehlers et al. | |
| 2013/0304061 | A1 | 11/2013 | Chang et al. | |
| 2014/0012314 | A1 * | 1/2014 | Dai | A61B 17/2804 606/207 |
| 2014/0058425 | A1 * | 2/2014 | Porat | A61B 17/2812 606/167 |
| 2014/0121508 | A1 * | 5/2014 | Latimer | A61B 5/4848 600/427 |
| 2014/0135820 | A1 | 5/2014 | Schaller et al. | |
| 2014/0221822 | A1 * | 8/2014 | Ehlers | A61B 5/061 600/424 |
| 2015/0077705 | A1 | 3/2015 | Artsyukhovich et al. | |

OTHER PUBLICATIONS

Solvay. "Technical Bulletin—Specialty Polymers—Optical Properties of Sulfone Polymers: A Unique Combination of Properties." Nov. 2014. [Retrieved on Apr. 26, 2019.] Retrieved from: <https://www.solvay.com/sites/g/files/srpend221 /files/2018-07/Sulfones-Optical-Properties_EN.pdf>.

Tao et al. "Microscope-Integrated Intraoperative OCT with Electrically Tunable Focus and Heads-Up Display for Imaging of Ophthalmic Surgical Maneuvers." Biomedical Optics Express. May 2014. vol. 5, No. 6. pp. 1877-1885.

\* cited by examiner

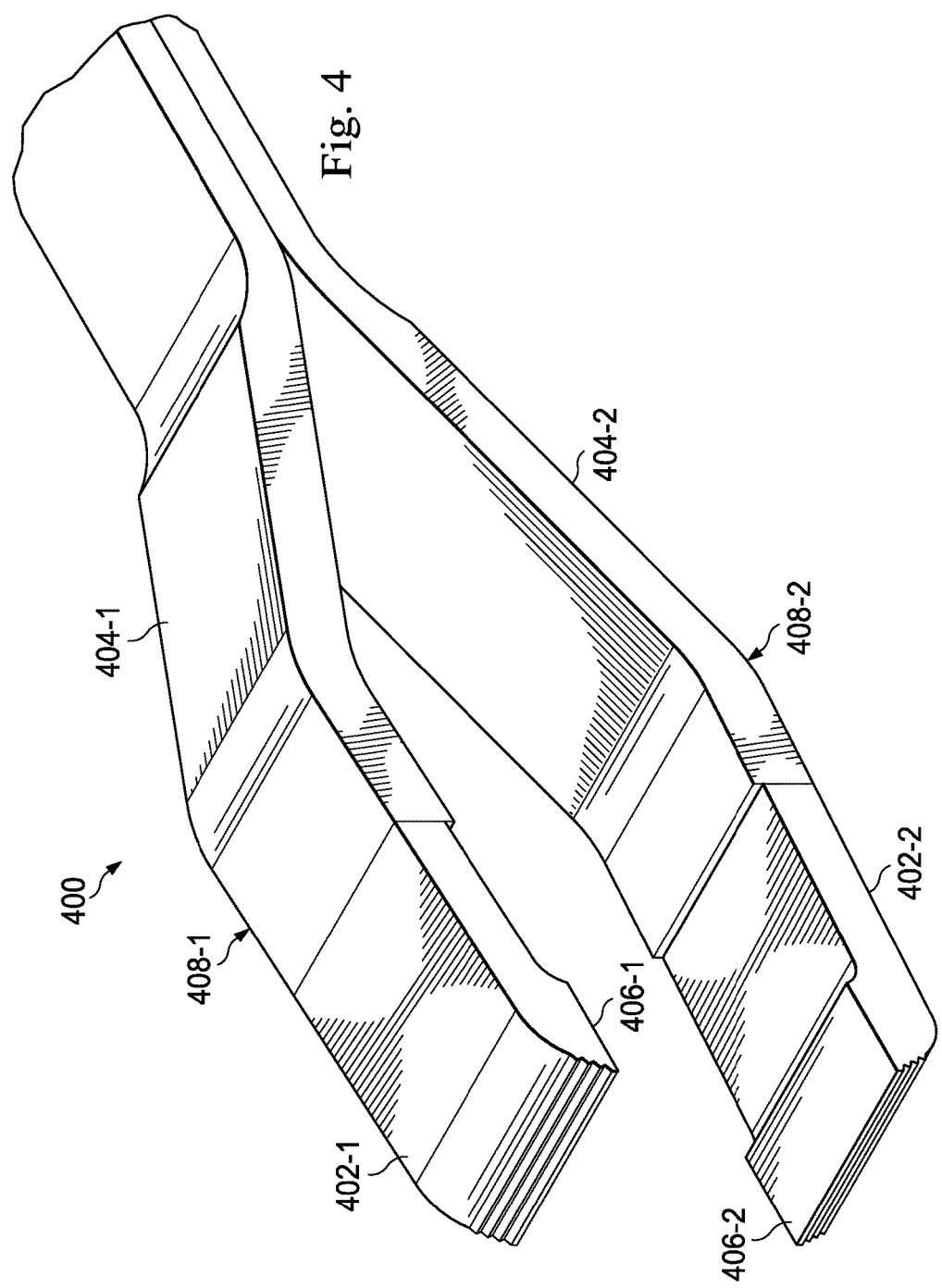

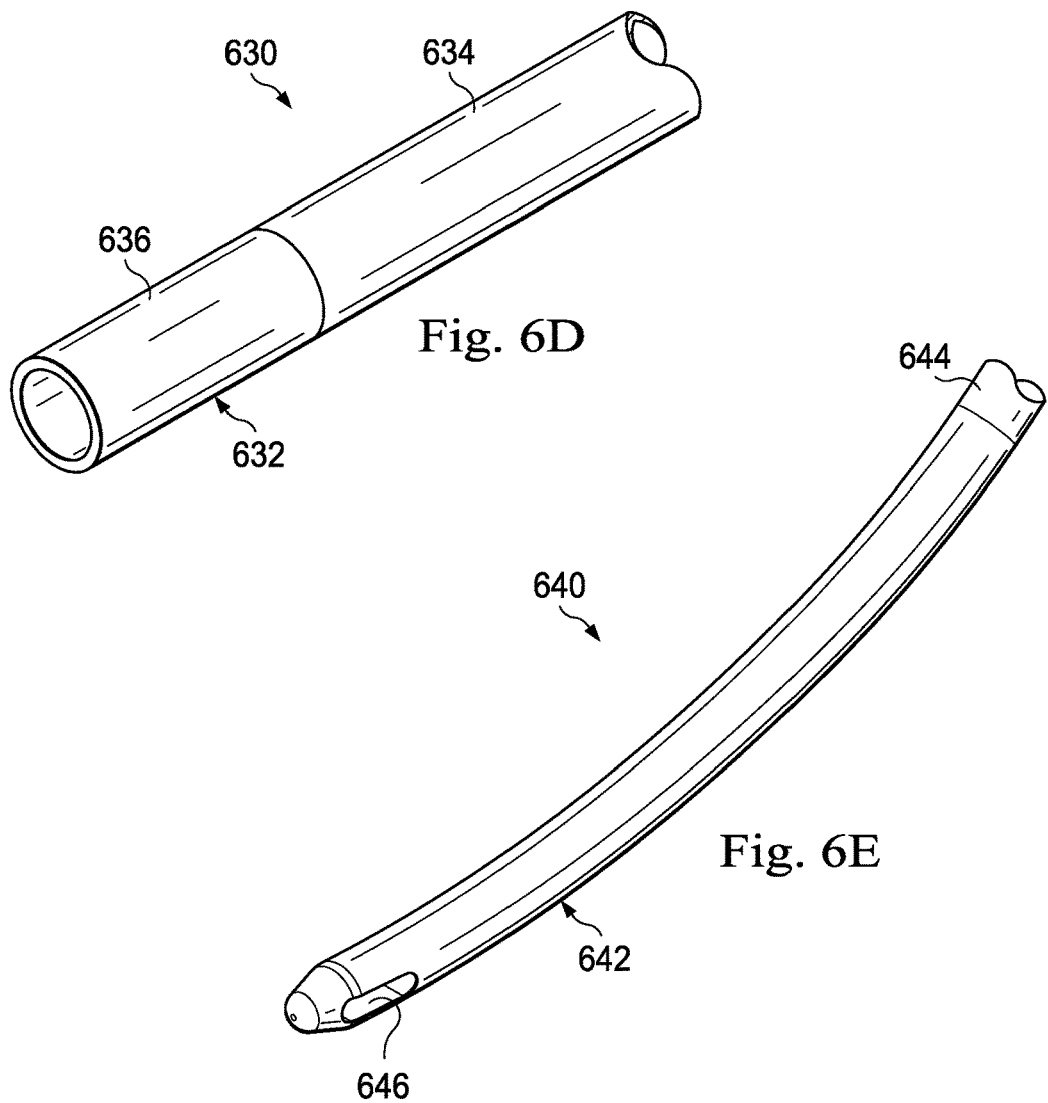
Fig. 6D
Fig. 6E
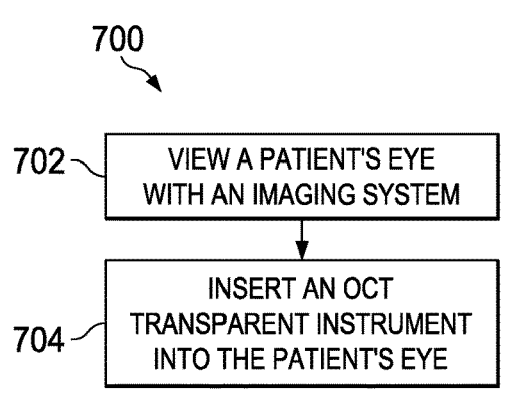
Fig. 7

OCT TRANSPARENT SURGICAL INSTRUMENTS AND METHODS

CROSS REFERENCE TO RELATED APPLICATIONS

This application claims the benefit of U.S. Provisional Application No. 62/012,073, filed Jun. 13, 2014, the entire contents of which are incorporated herein by reference.

TECHNICAL FIELD

The present disclosure relates to apparatuses and methods for ophthalmic medical procedures, and more particularly, to apparatuses and methods involving surgical instruments for such procedures.

BACKGROUND

Many microsurgical procedures require precision cutting and/or removal of various body tissues. For example, Internal Limiting Membrane (ILM) removal and epi-retinal membrane (ERM) removal are useful surgical treatments of different macular surface diseases. However, the surgical techniques for ILM and ERM peeling require skill and patience. Precise and carefully constructed surgical instruments are used for each segment of the surgical technique.

The surgical treatment includes grasping an edge of the membrane, and peeling the membrane. The surgical technique is a two-step procedure. First, the surgeon must gain an edge of the membrane. Some surgeons use a scraper to gain the edge. Next, the surgeon introduces a special forceps to grasp and peel the membrane. However, since each step requires patience and precision, a surgeon may sometimes scrape and then attempt to grasp the tissue multiple times during a single surgical procedure.

To aid the surgeon with such a surgical procedure, the surgeon may use an imaging system that presents a microscope view of the patient's eye. Thus, the surgeon can be provided with a close-up view of the forceps, or other tool, as well as the region of the eye that is of interest. In some cases, the surgeon may also be provided with an Optical Coherence Tomography (OCT) image of the region of the eye that is of interest. OCT imaging generally utilizes near-infrared light and is able to get images of tissue beneath the surface. There is a need for continued improvement in the use and operability of surgical systems and tools for various ophthalmic procedures. The systems and methods discussed herein are arranged to address one or more of the deficiencies in the prior art.

SUMMARY

According to one example, an ophthalmic instrument includes a shaft comprising a lumen. The instrument also includes a first arm extending from the lumen, the first arm having a first distal portion having a first flat tip. The instrument also includes a second arm extending from the lumen, the second arm having a second distal portion having a second flat tip that is positioned such that the second flat tip contacts the first flat tip when the first arm is forced towards the second arm. The first arm and the second arm comprise at least in part, a first material that is substantially transparent to electromagnetic radiation having a wavelength within a range of about 700-1200 nanometers (nm) and is substantially opaque to electromagnetic radiation having a wavelength within a range of about 400-700 nm.

An ophthalmic surgical system includes an image viewing system to display both a microscope image of a patient's eye and a cross-sectional Optical Coherence Tomography (OCT) image of the patient's eye. The system also includes a medical instrument comprising a shaft, and at least one arm extending from the shaft, the arm comprising at least in part, a first material that is substantially transparent to OCT imaging and substantially opaque to visible light such that the instrument appears in the microscope view of the patient's eye and does not block the cross-sectional OCT view.

A medical instrument includes a shaft and an arm extending from the shaft and having a distal tip. The arm includes at least in part a material that is substantially transparent to electromagnetic radiation having a wavelength within a range of about 700-1200 nanometers (nm) and is substantially opaque to electromagnetic radiation having a wavelength within a range of about 400-700 nm. The instrument also includes a marker feature formed on the tip of the arm. The marker feature is substantially opaque to electromagnetic radiation within the range such that an outline of the tip appears in an Optical Coherence Tomography (OCT) image of the instrument.

A method includes viewing a patient's eye with an imaging system, the imaging system configured to display a microscope image of the patient's eye overlaid with an OCT image of a cross-section of tissue of the patient's eye. The method further includes inserting a medical instrument into the patient's eye, the medical instrument comprising an arm that comprises at least in part, a material that is substantially transparent to electromagnetic radiation within a range of about 700-1200 nanometers such that electromagnetic radiation within the range is not blocked for the OCT image and the instrument is visible in the microscope view.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 4 is a diagram showing an illustrative surgical instrument having an OCT transparent distal portion according to one example incorporating the principles described herein.

FIGS. 6A-6E are diagrams showing illustrative OCT transparent surgical instruments according to one example incorporating the principles described herein.

FIG. 7 is a flowchart showing an illustrative method for using an OCT transparent surgical instrument according to one example incorporating the principles described herein.

DETAILED DESCRIPTION

Figure 1:
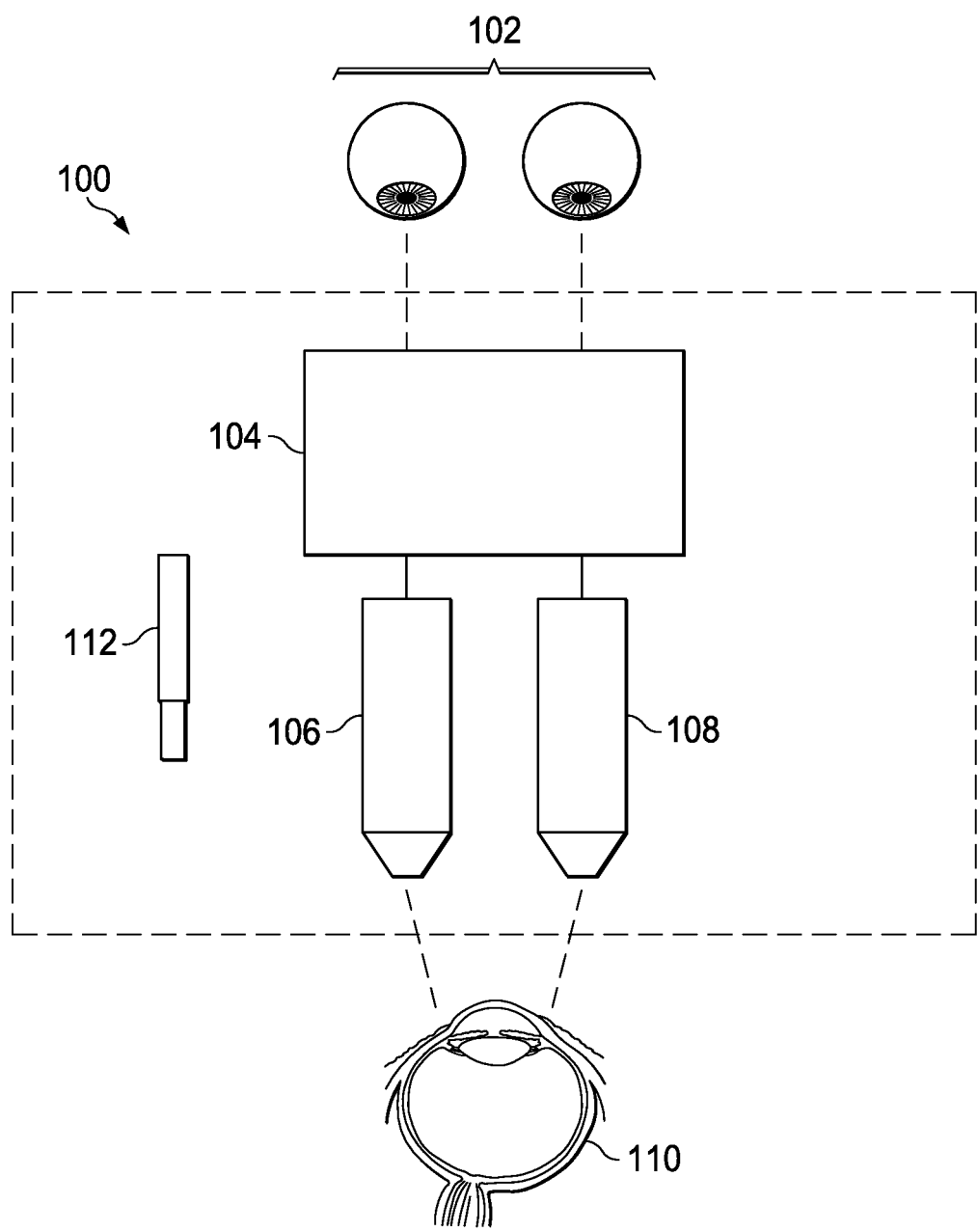
FIG. 1 is a diagram showing an illustrative ophthalmic surgical system according to one example incorporating the principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to OCT transparent surgical instruments that are usable in ophthalmic surgical procedures and associated methods. In these procedures, a surgeon may observe a surgical site, such as an eye of a patient, using both a microscope and an OCT imaging system. In some embodiments, the microscope is OCT compatible, and the microscope permits the surgeon to observe both a conventional microscope image and an OCT image while using a surgical instrument to perform an ophthalmic surgical procedure such as an ILM removal. The conventional microscope image is observed using light that is within the visible spectrum having a wavelength ranging between about 400 nanometers and 700 nanometers. The OCT image is generated using light in the near infrared range having a wavelength within a range of about 700 nanometers to 1200 nanometers. Light within this range will be referred to as light within the OCT spectrum. In some cases, the OCT image may provide a cross-sectional view of the region of interest within the eye and may be used to identify tissue below the outer surface tissue. Conventional surgical tools are visible both in the visible light spectrum and in the OCT light spectrum. Because of this, a conventional surgical tool will block the light within the OCT spectrum that is used by the OCT imaging system, thus blocking the entire view of the surgical site below the surface of the tissue.

The OCT transparent surgical instruments usable in ophthalmic surgical procedures and the associated methods described herein relate to surgical instruments that are opaque within the visible spectrum and are transparent in the OCT spectrum. Thus, during an ophthalmic surgical procedure, the surgeon can see the instrument through the microscope, but at the same time, the instrument is transparent to the surgeon in the OCT image. That is, the instrument will not block the OCT light. Thus, the surgeon may observe a substantially non-distorted cross-sectional OCT image of the region of interest within the patient's eye, even when the instrument is in place and in use.

FIG. 1 is a diagram showing an illustrative ophthalmic surgical system 100. According to the present example, the system 100 includes an image viewer 104, a microscope imaging system 106 and an OCT imaging system 108. Additionally, the system includes a surgical instrument 112 that is transparent within the OCT spectrum but opaque within the visible spectrum.

The microscope imaging system 106 obtains images of the patient's eye using light within the visible spectrum. The visible spectrum defines the wavelength range of light that is visible to the human eye. The visible spectrum includes electromagnetic radiation having a wavelength that is generally within a range of about 400 nanometers to 700 nanometers, though this wavelength range may vary slightly for different individuals. The microscope imaging system may use a system of lenses to provide a close-up view of the patient's eye or even a specific region of interest within the patient's eye. Such an image may then be provided to the image viewer 104.

The OCT imaging system 108 obtains OCT images of the patient's eye. It uses various techniques to obtain images of the patient's tissue beneath the surface of the tissue that are not able to be obtained from the use of standard visible light. This is done using light that is within the OCT spectrum. This range includes electromagnetic radiation having a wavelength between about 700 nanometers and 1200 nanometers. The OCT imaging system 108 may be used to obtain a cross-sectional view of the region of interest at which the surgeon is operating. Thus, the surgeon is able to see how interactions between the surgical instrument and the surface of an ILM affect the tissue below the surface of the ILM. Specifically, the surgeon can use the cross-sectional image to help avoid accidental damage to the underlying retina. In some examples, the OCT imaging system 108 is integrated with the conventional microscope imaging system 106. In some examples, however, the OCT imaging system 108 may be a separate apparatus that provides the OCT images to the image viewer 104.

The image viewer 104 displays to a surgeon 102 or other operator, the images obtained by both the microscope imaging system 106 and the OCT imaging system 108. The image viewer 104 may display the images in a variety of ways, such as on a monitor, display screen, on the microscope eyepiece, or in other ways. In one example, the microscope imaging system 106 may provide stereoscopic images formed of at least two images. The image viewer may display the at least two images to different eyes of the surgeon 102, thus creating a three dimensional effect.

Figure 2:
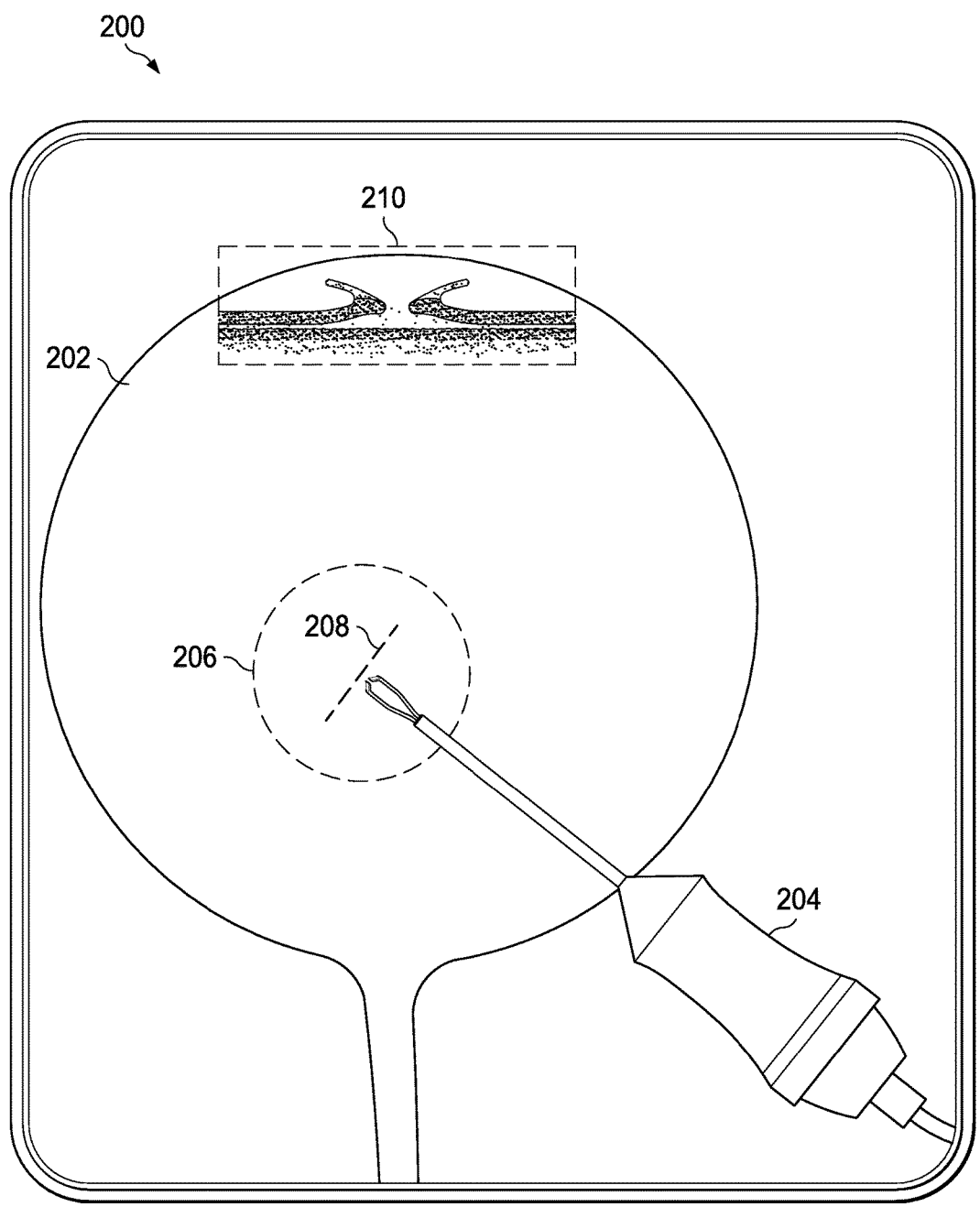
FIG. 2 is a diagram showing an illustrative image of a patient's eye as may be seen through an OCT-enabled microscope during a surgical procedure according to one example incorporating the principles described herein.

FIG. 2 is a diagram showing an illustrative combined microscope and OCT view 200 of a patient's eye as presented or displayed by the image viewer 104. According to the present example, the image viewer 104 (FIG. 1) overlays an OCT image 210 on a microscope image 202. Thus, the surgeon can view a potential region of interest 206 along with the surgical instrument 204 being used to operate within the region of interest 206. The dotted line 208 in FIG. 2 represents the cross-sectional line at which the cross-sectional OCT image 210 is taken. Thus, as can be seen, image viewer 104 projects the OCT image 210 onto the microscope image 202 in a manner permitting the surgeon to visually observe both images 202, 210 at once.

Figure 3:
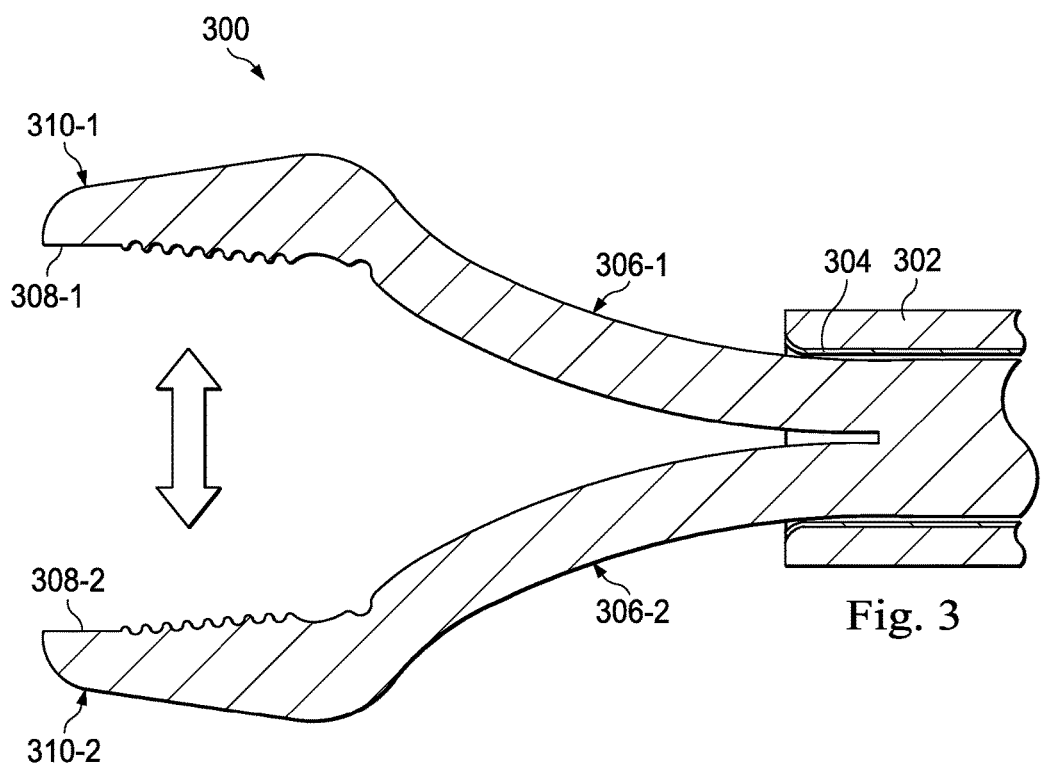
FIG. 3 is a diagram showing an illustrative OCT transparent surgical instrument according to one example incorporating the principles described herein.

FIG. 3 is a diagram showing an exemplary OCT transparent surgical instrument, as forceps 300. Although shown and described as forceps, other surgical instruments may be used, as will be apparent from the discussion below and the accompanying drawings. According to the present example, the forceps 300 in FIG. 3 includes a shaft 302 having a lumen 304 extending therethrough.

A first arm 306-1 and a second arm 306-2 extend from the lumen 304. The first arm 306-1 includes a distal end 310-1 having an inwardly facing first flat tip 308-1. The first flat tip 308-1 faces the second arm 306-2. The second arm 306-2 includes a distal end 310-2 having an inwardly facing second flat tip 308-2. The second flat tip 308-2 faces the first arm 306-1. Thus, when the two arms 306-1, 306-2 are forced towards each other, the two flat tips 308-1, 308-2 squeeze together and make contact with each other. As such the forceps 300 may be useful in many surgical procedures, including ILM and ERM removal. In some embodiments, the first flat tip 308-1 may be angled towards the second flat tip 308-2. Likewise, the second flat tip 308-2 may be angled towards the first flat tip 308-1.

In the exemplary embodiment shown in FIG. 3, the forceps are biased to the open condition. It may be closed to grasp tissue or other elements by moving the shaft 302 in an axial direction relative to the arms 306-1, 306-2. As the shaft 302 moves toward the distal ends of the arms 306-1, 306-2, the leading edge of the shaft 302 forces the two arms 306-1, 306-2 towards each other. Specifically, the shaft 302 may act as a sleeve that presses the arms together as it moves to cover the arms 306-1, 306-2. As the arms 306-1, 306-2 extend further from the shaft 302, they may be biased to automatically expand apart.

The forceps 300 is made of a material that is substantially transparent to electromagnetic radiation having a wavelength within a range between about 700 nanometers and 1200 nanometers, and are also substantially opaque to light in the visible spectrum having a wavelength within a range between about 400 nanometers and 700 nanometers. In one example, such a material may be a polycarbonate material. Some examples of polycarbonate materials that are transparent to light within the OCT spectrum and that are opaque to light within the visible spectrum include Makrolon® and Apec® manufactured by Bayer AG, Calibre™ manufactured by Styron, and Lexan® manufactured by Sabic. Other materials that are transparent to electromagnetic radiation within the OCT spectrum and that are opaque to light within the visible spectrum are contemplated as well. As described above, use of such material allows the surgical instrument to be visible within a microscope view but transparent to OCT imaging.

Although shown with the shaft 302 and the arms 306 being formed of an OCT transparent material, in some embodiments, less than the entire surgical instrument is formed of the OCT transparent material. For example, some embodiments include the shaft 302 formed of a non-OCT transparent material, such as a metal material, and the arms 306 are formed of the OCT transparent material. Other arrangements are also contemplated.

FIG. 4 is a diagram showing an illustrative surgical instrument 400 having an OCT transparent distal portion. According to the present example, the surgical instrument 400 is an alternative forceps and includes a first arm 408-1 and a second arm 408-2. The first arm 408-1 includes a proximal portion 404-1 and a distal portion 402-1. Likewise, the second arm 408-2 includes a proximal portion 404-2 and a distal portion 402-2. In this exemplary embodiment, the distal portions 402-1, 402-2 respectively include an inward pointing portion 406-1, 406-2.

According to the present example, the proximal portions 404-1, 404-2 are made of a material that is opaque to light within both the visible spectrum and the OCT spectrum. For example, the proximal portions 404-1, 404-2 may be made from a metal material. Other materials opaque in both the visible and OCT spectrums are contemplated as well. The distal portions 402-1, 402-2 are made of a material that is transparent within the OCT spectrum. Because of this, a surgeon may see the instrument body in the OCT image, but the portion of the instrument engaging tissue in the area of interest is transparent to the OCT image. Thus, the surgeon can view the tissue in the OCT image without the shadowing effects of the instrument tip. Such an OCT compatible material may include a polycarbonate material as described above.

Figure 5A:
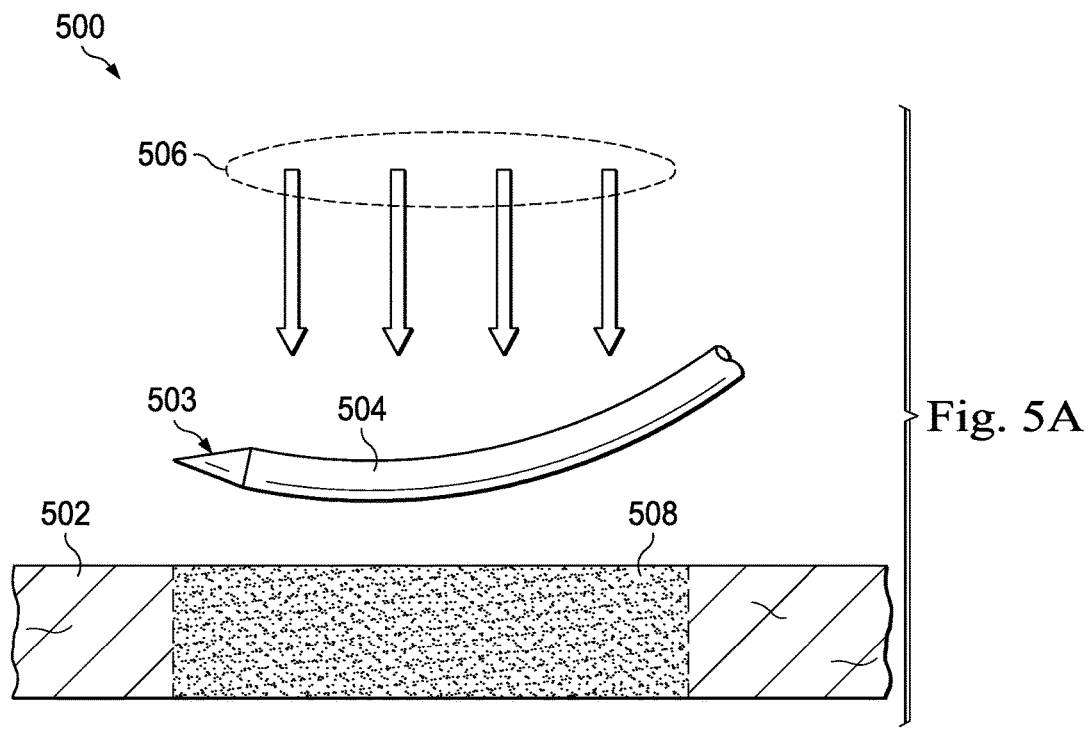
FIG. 5A is a diagram showing a conventional surgical instrument within a stylized OCT image and the resulting shadow restricting visualization of the tissue in the OCT image.
Figure 5B:
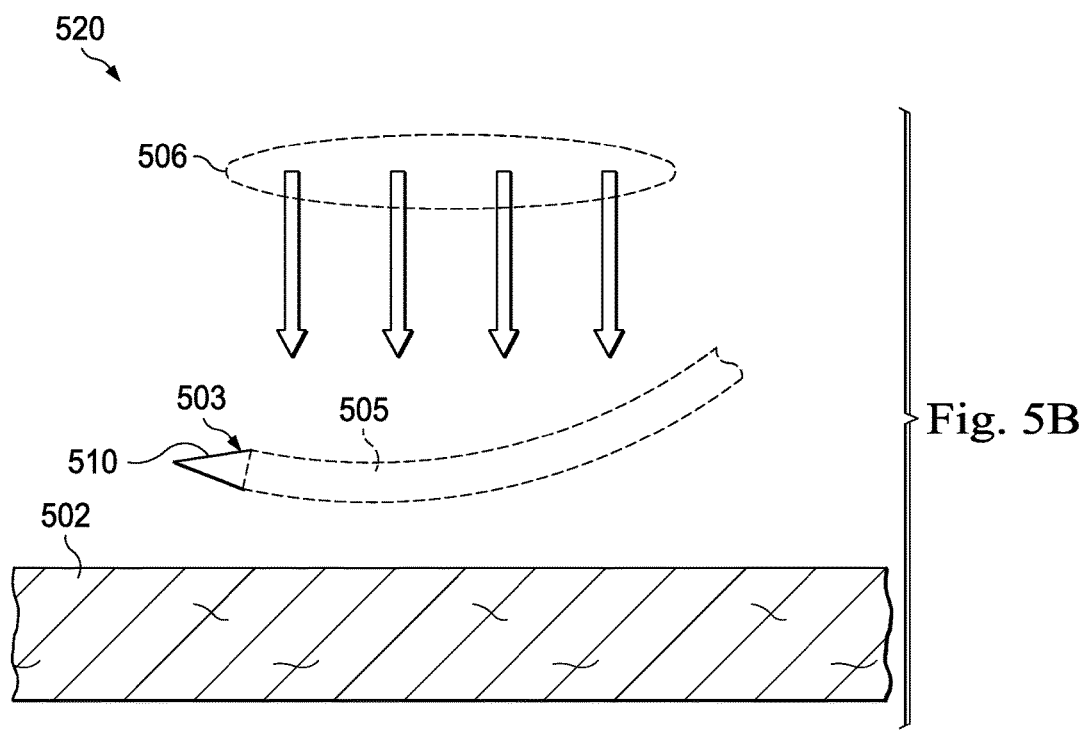
FIG. 5B is a diagram showing a surgical instrument within an OCT image according to one example incorporating the principles described herein and the resulting shadow of the tissue in the OCT image.

FIGS. 5A and 5B are diagrams showing surgical instruments within an OCT image for comparison. FIG. 5A illustrates an OCT image 500 wherein an instrument 504 is not made of a material that is transparent to light within the OCT imaging spectrum. That is, the instrument 504 is made of a conventional material, such as a metal material, for example. Because light 506 within the OCT spectrum that is emitted from the OCT imaging system 108 (FIG. 1) is blocked by the instrument 504, the tissue 502 below the instrument 504 is not imaged properly in an OCT image. The blocked light 506 results in an OCT image with a shadowed out region 508 within the tissue 502 below the instrument 504.

FIG. 5B, in contrast, shows an OCT image 520 with an instrument 505 that is transparent to light within the OCT spectrum. Thus, light 506 from the OCT imaging system 108 (FIG. 1) is able pass through the instrument 505 and into the tissue. The OCT imaging system 108 can then obtain reflected light usable to construct an image of the tissue 502 beneath the tissue surface.

Some embodiments of the surgical instrument tip 503 include various markers or features 510 that partially reflect light within the OCT spectrum, thus causing it to appear within the OCT spectrum without causing any shadowing. For example, the tip 503 of the instrument may include various spots or gratings that partially reflect light within the OCT spectrum. Some embodiments of the features 510 also include a coating with a material that has an index of refraction that is different than that of water. In still other instances, the markers 510 may be formed from or include a material that has an index of refraction different than a material introduced into the eye during a surgical procedure. Examples of such materials may include, but are not limited to a plastic coating with structuring or texturing, silicon dioxide (SiO2), titanium dioxide (TiO2), or other transparent material with a different index of refraction. In an OCT image, such features 510 appear as an outline of the instrument tip 510. It may be useful to a surgeon to see where the instrument tip 510 is visible within the OCT image for reference during the procedure, while minimizing or substantially eliminating any shadowing.

Figure 6A:
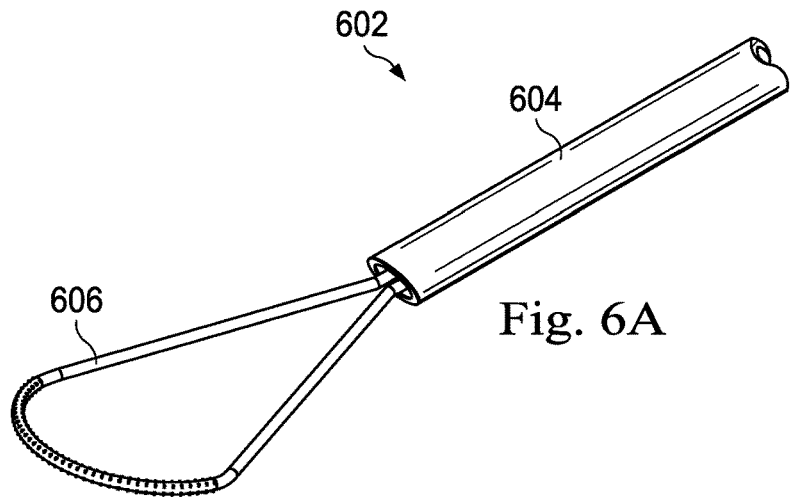

FIGS. 6A-6E are diagrams showing illustrative OCT transparent surgical instruments. FIG. 6A is a diagram showing an illustrative scraping surgical instrument 600. According to the present example, the scraping surgical instrument 600 includes a shaft 604 and a distal portion 602 that includes a wire 606 extending from the shaft 604. The shaft 604 is made of an opaque material such as a metal or standard plastic material. The wire 606 is made from an OCT transparent material.

Figure 6B:
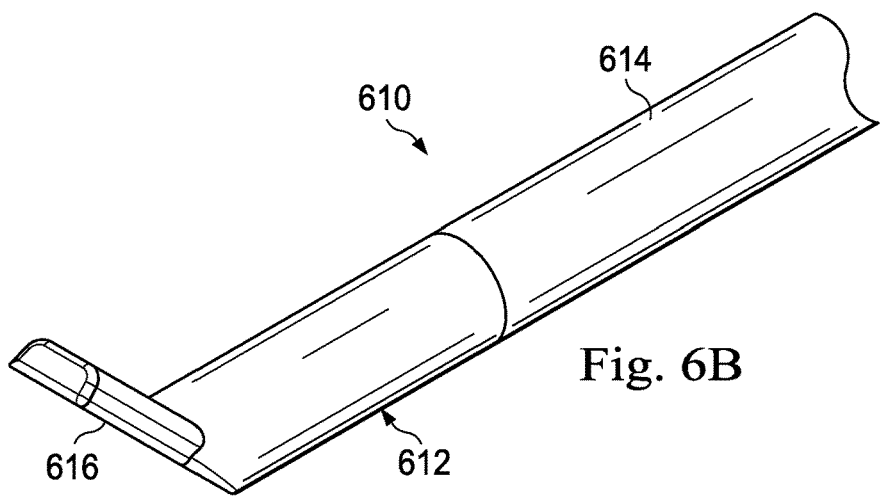

FIG. 6B is a diagram showing an illustrative spatula surgical instrument 610. According to the present example, the spatula surgical instrument 610 includes a proximal portion 614 and a distal portion 612. The distal portion 612 includes a spatula feature 616 that is angled with respect to the proximal portion 614. The proximal portion 614 is made from an opaque material such as a metal or a standard plastic material. The distal portion 612 is made from an OCT transparent material.

Figure 6C:
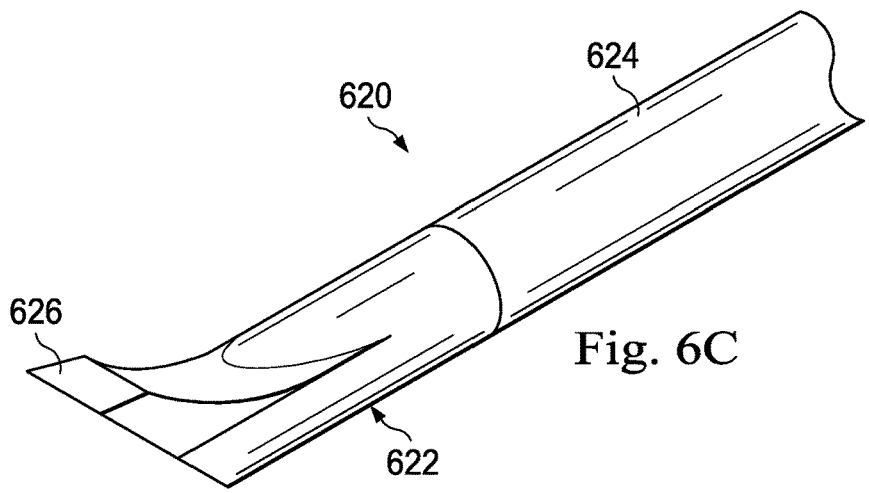

FIG. 6C is a diagram showing an illustrative pick surgical instrument 620. According to the present example, the pick surgical instrument 620 includes a proximal portion 624 and a distal portion 622. The distal portion 622 includes a pick feature 626 that is angled with respect to the proximal portion 624. The proximal portion 624 is made from an opaque material such as a metal or a standard plastic material. The distal portion 622 is made from an OCT transparent material.

FIG. 6D is a diagram showing an illustrative soft tip surgical instrument 630. According to the present example, the soft tip surgical instrument 630 includes a proximal portion 634 and a distal portion 632. The distal portion 632 includes a hollow soft tip feature 636. The proximal portion 634 is made from an opaque material such as a metal or a standard plastic material. The distal portion 632 is made from an OCT transparent material.

FIG. 6E is a diagram showing an illustrative aspirator surgical instrument 640. According to the present example, the aspirator surgical instrument 640 includes a proximal portion 644 and a distal portion 642. The distal portion 642 includes a hollow tube having an opening 646 at the end. The hollow interior of the distal portion 642 may extend through the proximal portion 644 such that fluid can be aspirated through the opening 646 and out of the proximal end of the surgical instrument 640. The proximal portion 644 is made from an opaque material such as a metal or a standard plastic material. The distal portion 642 is made from an OCT transparent material.

FIG. 7 is a flowchart showing an illustrative method 700 for using an OCT transparent surgical instrument. According to the present example, at step 702, the method 700 includes viewing a patient's eye with a surgical system, such as the ophthalmic surgical system 100. As described above, viewing the patient's eye may include looking at an image or images taken with light from the visible spectrum and from the OCT spectrum. Such an image taken with light from the spectrum may be through a microscope, including a stereoscopic microscope. Additionally, an image taken with light from the OCT spectrum may include looking at a cross-sectional OCT image of the region of interest within the eye.

At step 704, the method includes inserting an OCT transparent instrument into the patient's eye. In one example, the OCT transparent instrument is a tool such as forceps used for performing an ILM removal. In other examples, any of the other instruments disclosed herein or otherwise arranged to be OCT transparent may be inserted into the patient's eye. As described above, the OCT transparent instrument may be opaque to light within the visible spectrum so that the instrument appears on the image taken with light from the visible spectrum, such as the microscope image. But, because the instrument is OCT transparent, it does not block light within the OCT spectrum. Thus, an OCT image of the region of interest can still be obtained even when the instrument is directly above that region of interest.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. An ophthalmic instrument comprising:
a shaft comprising a lumen;
a rod extending through the lumen of the shaft;
a first arm coupled to a distal end of the rod and extending from the lumen, the first arm having a first distal portion having a first flat tip; and
a second arm coupled to the distal end the rod and extending from the lumen, the second arm having a second distal portion having a second flat tip that is positioned such that the second flat tip contacts the first flat tip when the first arm is forced towards the second arm;
wherein the first arm and the second arm comprise at least in part, a first material that is transparent to electromagnetic radiation having a wavelength within a range of about 700-1200 nanometers (nm) and is opaque to electromagnetic radiation having a wavelength within a range of about 400-700 nm,
wherein the first distal portion of the first arm and the second distal portion of the second arm comprise the first material that is transparent to electromagnetic radiation having a wavelength within a range of about 700-1200 nm,
wherein the first arm and the second arm each comprise a proximal portion formed of a second material that is opaque to electromagnetic radiation within the range of 700-1200 nanometers (nm), the first arm coupled to the distal end of the rod at the proximal portion of the first arm and the second arm coupled to the distal end of the rod at the proximal end of the second rod, and
wherein the first arm and the second arm each comprise a marker feature disposed at the distal end of the first arm and at the distal end of the second arm, the marker feature being partially reflective to electromagnetic radiation within the range of about 700-1200 nm such that an outline of the tip appears in an Optical Coherence Tomography (OCT) image of the instrument.
2. The instrument of claim 1, wherein the first flat tip is angled towards the second arm and the second flat tip is angled towards the first arm.
3. The instrument of claim 1, wherein the second material that is opaque to electromagnetic radiation comprises a metal material.
4. The instrument of claim 1, wherein the marker feature comprises a material having an index of refraction that is different than an index of refraction of water.
5. The instrument of claim 1, wherein the marker feature comprises a material having an index of refraction that is different from an index of refraction of a material introduced into an eye during a surgical procedure.
6. The instrument of claim 1, wherein the marker feature comprises spots formed on the distal ends of the first arm and the second arm.
7. The instrument of claim 1, wherein the first material comprises a polycarbonate material.

* * * * *